United States Patent [19]

Bessler

[11] Patent Number: 4,883,072
[45] Date of Patent: Nov. 28, 1989

[54] MOUTH APPLIANCE FOR ASSISTING IN WEIGHT CONTROL

[76] Inventor: Edward W. Bessler, 8 Rosemont Ave., Fort Mitchell, Ky. 41017

[21] Appl. No.: 309,404

[22] Filed: Feb. 13, 1989

[51] Int. Cl.4 .............................................. A61F 13/12
[52] U.S. Cl. ...................................... 128/857; 128/859
[58] Field of Search ............... 128/857, 859, 860, 858, 128/861

[56] References Cited

U.S. PATENT DOCUMENTS

| | | | |
|---|---|---|---|
| 1,297,842 | 3/1919 | Harllee | 128/857 |
| 1,354,652 | 10/1920 | Jefferies | 128/857 |
| 2,667,869 | 2/1954 | D'elia | 128/857 |
| 4,344,424 | 8/1982 | Barmby | 128/857 |
| 4,711,237 | 12/1987 | Kaiser | 128/859 |

Primary Examiner—Richard J. Johnson
Assistant Examiner—Charles H. Sam
Attorney, Agent, or Firm—Irwin P. Garfinkle

[57] ABSTRACT

A disposable appliance for inhibiting the intake of food is disclosed. The appliance comprises first and second spaced pressure sensitive adhesive pads applied to the cheeks of a user at the corners of the user's mouth, the ends of one or more bands being connected to the pads. The bands are arcuate, so that they arch over the junction of the lips of the user. The appliance permits normal breathing and speech, while at the same time inhibiting the intake of food through the lips.

6 Claims, 1 Drawing Sheet

MOUTH APPLIANCE FOR ASSISTING IN WEIGHT CONTROL

This invention is directed to a simple, disposable appliance for aiding persons on weight reduction diets to control their food intake, and is an improvement over my earlier filed application entitled Appliance For Assisting In Weight Control, application Ser. No. 168,466. filed Mar. 15, 1988.

BRIEF STATEMENT OF THE INVENTION

Briefly stated, my invention utilizes two pads of pressure sensitive adhesive tape which are adhered to the user's cheeks adjacent the corners of the user's lips, the ends of one or more elongated arcuate bands being affixed to the pads, the bands arching forward from the pads and bridging over the user's mouth at the junction of the user's upper and lower lips, without making contact therewith. The arcuate bands may be made from any thin, elongated material which is capable of being formed into an arc, for example, metal, plastic, fiberglass or other similar material. The bands may be flexible or rigid, so long as they are light weight and formed with an arch or bow sufficient to bridge the user's mouth without making contact therewith.

This invention is an improvement over my prior invention in that when worn by the user, the bands arching over the lips do not in any material way inhibit motion of the mouth and lips. My prior invention, on the other hand, used elastic lines, or lines with slack which imposed some inhibition on lip movement. The device is normally disposable after each use.

BACKGROUND OF THE INVENTION

In accordance with my earlier filed invention, I disclosed a simple arrangement of two plastic strips adhered, respectively to the upper and lower lips of the user, and interconnected by food intake inhibiting lines. In essence, that invention simulated the idea of sewing the user's lips together, but it did so in a manner which permitted relatively normal speech, plus limited food and liquid intake, and which was removable by the user at the user's will.

The present invention is a modification of my earlier invention. Instead of applying adhesive strips above and below the lips, and interconnecting the strips with a plurality of non-rigid food intake inhibiting line oriented generally transverse to the strips, the present invention utilizes pads which are adhered to the user's cheeks at the corners of his or her mouth. Arcuate food intake inhibiting bands connected to the pads are oriented from side to side, arching over the junction of the upper and lower lips, and out of contact with the lips.

The primary advantage of the present invention over my earlier invention is that normal speech and mouth movement are uninhibited, while the interposition of bands parallel to the junction of the lips provides a physical block which will inhibit the intake of food through the mouth. In addition, the new appliance provides enhanced comfort for the user, since the bands are out of contact with the user's lips, and the device is less conspicuous when worn.

The present invention uses small adhesive pads in the form of short strips, ovals or circles secured to the corners of the mouth to support horizontal bands which extend over and across the lips. The bands extending across the mouth opening have been found comfortable to wear, and serve as a positive reinforcement of the user's will power to control food intake.

There is a number of prior art patents in the field of diet control devices known to the inventor, but none is believed to utilize the inventive features disclosed and claimed in this application. Brown et al., International Application Publication No. WO 86/01706 shows a dental appliance worn in the mouth of the user for disrupting natural masticating and thereby inhibiting eating. Stubbs U.S. Pat. Nos. 3,224,442 and 3,818,906 show devices worn in the user's mouth, and which provide an inward tab that can be flipped back and forth by the tongue to stimulate saliva, and hence reduce the desire for food. The Stubbs and Brown devices differ from the present invention in that they are worn in the mouth and alter conditions in the user's mouth, whereas the present invention is worn outside of the mouth, and provides a simple block to the introduction of food.

Barmby, U.S. Pat. No. 4,344,424 show an external anti-eating face mask which provides a rigid screen over the wearer's mouth. Barmby's device differs from the present invention in that it comprises a rigid frame structure which totally blocks the intake of food. The present invention provides arcuate bands connected between pressure sensitive adhesive pads applied to the face.

There are several patents of relevance to pressure sensitive adhesive tape. Thomas U.S. Pat. No. 3,677,250 which shows pressure sensitive adhesive tape device for anchoring tubes to a patient's skin. Jefferies U.S. Pat. No. 1,354,652 shows an adhesive tape device applied to the lips to seal the user's mouth shut. Selix U.S. Pat. No. 3,368,564 shows a tube anchoring device which is adhered to a patients skin. None of these patents has any relevance to diet control devices.

Patterson Canadian Pat. No. 725,336 shows a hockey mouth guard secured across the mouth of a hockey player by connecting the protector to straps on the helmet. This patent does not show the idea of diet control, nor does it shown the suspension of arcuate bands from pressure sensitive adhesive pads applied to the cheeks of a user.

SUMMARY OF THE INVENTION

This invention is an appliance comprising first and second pressure sensitive adhesive pads applied to the user's cheeks at the corner of the user's mouth, the pads serving to support one or more food intake inhibiting bands extending from side to side between the corners of the mouth. The inhibiting bands are elongated, arcuate structures which arch over the lips of the user and bridge the junction between the user's lips to inhibit food intake by providing a mechanical and emotional barrier, while at the same time permitting normal mouth movements for uninhibited speech and mastication.

DESCRIPTION OF THE EXEMPLARY EMBODIMENTS

Figure 1:
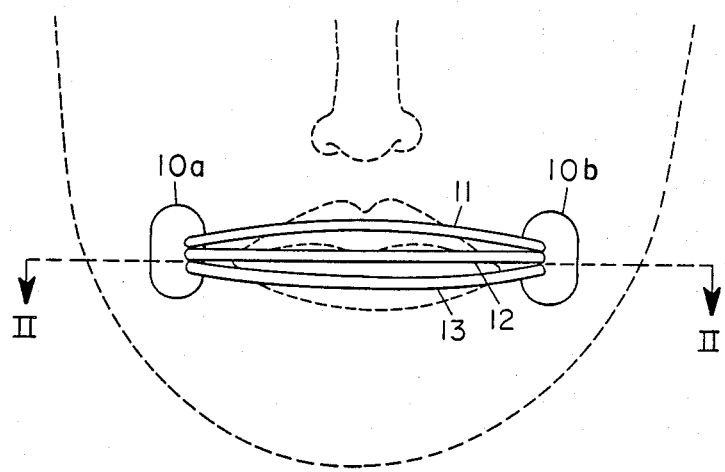
FIG. 1 shows an exemplary embodiment of the invention applied across the lips of a user.
Figure 3:
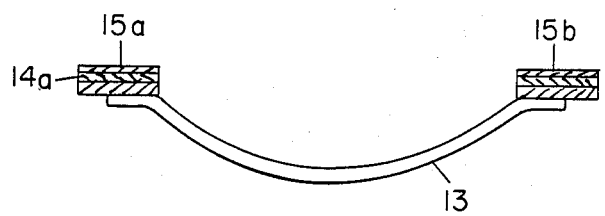
FIG. 3 is a view taken through the line 3—3 in FIG. 2.

Referring to FIG. 1, the diet control appliance consists of two identical pads 10a and 10b applied to the cheeks of a user adjacent the corners of the user's mouth. A plurality of elongated bands 11, 12 and 13 are bonded or otherwise secured at their ends to the pads 10a and 10b by any suitable means. As shown in FIG. 3 the bands 11, 12, and 13 are bowed, so that when the device is mounted on the cheeks of the user, the bands arch over and bridge the junction of the user's lips, normally without making contact therewith.

The pads 10a and 10b are constructed from sheet material with a layer of adhesive material 14a and 14b applied to the bottom of each. Conventional adhesive cover sheets 15a and 15b applied over the adhesive material prevents premature sticking prior to use, and are easily peeled away. The elongated connecting bands 11, 12 and 13 are free of any adhesive material, except where bonded to the pads.

The two pads 10a and 10b may be cut from various sheet materials, and any material capable of supporting the bands will be suitable, for example rubber or cloth reinforced with fiber glass. In an actual reduction to practise of the invention, a plastic tape material was used. The particular shape of the pads is illustrative, and any shape including circular, square, rectangular or oval can achieve equivalent results.

Figure 2:
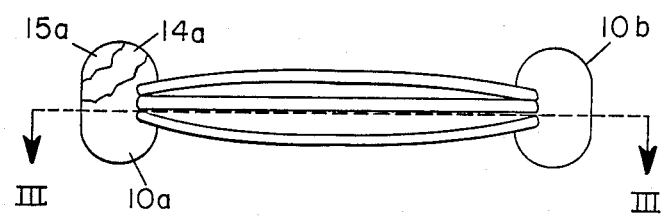
FIG. 2 is a view of the embodiment of FIG. 1 partially cut away, and showing details of construction of the invention.
Figure 4:
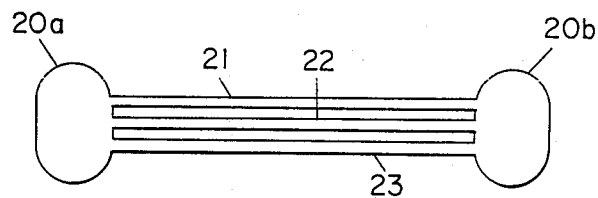
FIG. 4 is a second embodiment of the invention.

FIG. 4 is a view of an embodiment of the invention which is essentially identical to the embodiment of FIGS. 1 to 3, except that in this embodiment, pads 20a and 20b are made from a material which can be formed into a contoured structure, and the bowed bands 21, 22 and 23 are integral with the pads.

THE USE OF THE INVENTION

To use the food intake control device, the dieter first peels off the cover sheets 15a and 15b, and then applies the pads 10a and 10b to the cheeks at the opposite corners of the lips. Because the bands arch over the user's lips and make no contact therewith the ability of the user to open his lips and to speak and breathe through his mouth is unimpaired. However the bands 11, 12 and 13 will provide an effective mechanical block, and will thereby severely inhibit the attempt to place food in the mouth without removing the appliance.

While the invention is illustrated as having three bands 11, 12 and 13, it will be understood that the number may be varied. The optimum number will depend on a number of factors including the size of the bands, the size of the user's mouth, and the cosmetics. The invention was reduced to practise using 1 and 3 bands.

Since the device is disposable, it is intended to be worn only once, and the user may take it off at any time, and replace it when he or she feels the urge to eat.

In summary, I have invented an appliance which will serve to help dieters with less than sufficient will power to control their eating habits, especially between meals, and to achieve the weight loss recommended for them.

Various modifications and adaptations will be apparent to persons skilled in the art, and it is intended, therefore, that this invention be limited only by the appended claims as interpretted in the light of the prior art.

I claim:

1. Apparatus for assisting in the reduction of food intake on the part of a person using the same, the combination comprising:

first and second pads;

a pressure sensitive adhesive on one side of said pads for securing said pads to a user's cheeks adjacent the corners of the mouth of the user;

at least one narrow band curved to form an arch, the opposite ends of said band being connected to said first and second pads, respectively, the arch of said band projecting from the user's cheeks and arching over the junction of the user's lips out of contact therewith, said bands thereby inhibiting the passage of food through the lips of the user when the pads are secured to the user's cheeks, but not interfering with normal movement of the lips.

2. The invention as defined in claim 1, and a protective, peelable backing on said adhesive.

3. The invention as defined in claim 1, wherein there are a plurality of arcuate bands connected between said first and second pads.

4. The invention as defined in claim 1 wherein said bands are integral with said pads.

5. The invention as defined in claim 4, and a protective, peelable backing on said adhesive.

6. The invention as defined in claim 5, wherein there are a plurality of arcuate bands between said first and second pads.

* * * * *